United States Patent [19]

Zenno et al.

[11] Patent Number: 5,484,723
[45] Date of Patent: Jan. 16, 1996

[54] **FLAVIN REDUCTASE GENE FROM *VIBRIO FISCHERI***

[75] Inventors: Shuhei Zenno, Yokohamashi; Kaoru Saigo, Tokyo, both of Japan

[73] Assignee: Chisso Corporation, Osaka, Japan

[21] Appl. No.: 266,570

[22] Filed: Jun. 28, 1994

[30] Foreign Application Priority Data

Jun. 28, 1993 [JP] Japan .................................. 5-181850

[51] Int. Cl.$^6$ .................................................. C12N 9/02
[52] U.S. Cl. ................... 435/189; 435/252.3; 435/320.1; 536/23.2
[58] Field of Search .............................. 435/189, 252.3, 435/69.1, 172.3, 320.1; 536/23.2

[56] References Cited

PUBLICATIONS

Zenno et al. 1994 J. Bacteriology 176: 3544–3551.
Spyrou et al. 1991 J. Bacteriology 173: 3673–3679.

*Primary Examiner*—Robert A. Wax
*Assistant Examiner*—Lisa J. Hobbs
*Attorney, Agent, or Firm*—Leydig, Voit & Mayer

[57] ABSTRACT

A flavin reductase gene is provided having the nucleotide sequence of SEQ ID NO:1, wherein the sequence is displayed in numbered triplets of capital letters, which numbers proceed sequentially from left to right and from the 5' terminus to the 3' terminus; the sequence of capital letters represent the purine and pyrimidine bases of the nucleotide sequence, as follows:

A is adenine; G is guanine; C is cytosine; T is thymine;

R is A or G; Y is T or C; N is A, T, C, or G; H is A, C, or T; and M is A or C;

wherein triplet number 237 thereof is TAA or TAG or TGA; and wherein further:

for triplets numbered 13, 21, 22, 36, 63, 85, 92, 111, 112, 126, 140, 150, 156, 186, 196, and 228, if the 3' nucleotide of a triplet is A or G, then the 5' nucleotide of the triplet is T or C, or if the 3' nucleotide of a triplet is T or C, then the 5' nucleotide of the triplet is C; and if the 5' nucleotide of a triplet is C, then the 3' nucleotide of the triplet is A, T, C, or G, or if the 5' nucleotide of a triplet is T, then the 3' nucleotide of the triplet is A or G;

for triplets numbered 19, 46, 56, 103, 108, 123, 145, 206, and 214, if the 3' nucleotide of a triplet is T or C, then the 5' nucleotide of the triplet is A or C, or if the 3' nucleotide of a triplet is T or C, then the 5' nucleotide of the triplet is C; and if the 5' nucleotide of a triplet is G, then the 3' nucleotide of the triplet is A, T, C, or G, or if the 5' nucleotide of a triplet is A, then the 3' nucleotide of the triplet is A or G.

8 Claims, 2 Drawing Sheets

FRE3 (21mer):

```
N  -Gln  Tyr  Leu  Met  Val  Val  Met-C
5' -CAA, TAT, TTT, ATG, GTT, GTT, ATG-3'
        G    C    C    C         C
                       A         A
                       G         G
```

FRE4 (20mer):

```
N  -Ala  Gly  Arg  Phe  Glu  Met  Ala-C
3' -CGA, CCA, GCA, AAA, CTT, TAC, CG-5'
        G    G    T    G         C
        T    T    T
        C    C    C
```

FLAVIN REDUCTASE GENE FROM *VIBRIO FISCHERI*

BACKGROUND OF THE INVENTION

1. Field of the Invention

This invention relates to a flavin reductase gene from a luminescent bacterium Vibrio fischeri, a flavin reductase enzyme, a recombinant vector containing the gene and a bacterium containing the recombinant vector.

2. Description of the Related Art

An enzyme luciferase from a luminescent bacterium forms an oxidized flavin mononucleotide (hereinafter referred to as FMN) and a long chain fatty acid, using as substrates, a reduced flavin mononucleotide, (hereinafter referred to as $FMNH_2$) and a long chain fatty aldehyde and in the presence of the enzyme, and at that time, catalyzes a blue color-luminescence reaction.

In the cell, the substrate $FMNH_2$ used in this reaction is supplied from a reduced nicotinamide adenine dinucleotide : flavin mononucleotide (NADH : FMN) reductase and a reduced nicotinamide adenine dinucleotide phosphate: flavin mononucleotide (NADPH : FMN) reductase, and the long chain fatty aldehyde is supplied from a fatty acid reductase complex.

Recently, Spyrou et al. isolated a flavin reductase gene from Escherichia coli and clarified its primary structure and discloses it in [Spyrou, G., Haggard-Ljungquist, E., Krook, M., Jornvall, H., Nilsson, E. & Reichard, P. (1991), J. Bacteriol. 173, 3673–3679].

The present inventors have also already isolated an FMN reductase gene of a luminescent bacterium, Vibrio fischeri and have determined its nucleotide sequence. Further, we have succeeded in expressing the gene in Escherichia coli (Japanese patent application No. Hei 03-351,717). Further, we have isolated a flavin reductase gene from a luminescent bacterium, Xenorhabdus luminescens and have succeeded in its expression in Escherichia coli (Japanese patent application No. Hei 04-279029). This time, we have isolated a novel flavin reductase gene distinct from the above one (the contents corresponding to the present application).

$FMNH_2$ is easily and instantaneously autoxidized in air and converted into FMN. In order to make the luminescence ability of the bacterial luciferase exhibit up to the most, it is necessary to always continuously supply the $FMNH_2$ as the substrate, and FMN reductase is most important for attaining the object.

As described above, this enzyme couples with the bacterial luciferase and catalyzes the reaction of converting FMN as the product of the luciferase reaction into $FMNH_2$; hence when the luciferase is made coexistent with FMN reductase in the reaction system, it is possible to maintain the luminescence reaction. Namely, since the bacterial luciferase turns over many time, luminescence continues as far as a large excess of a long chain aldehyde is present in the reaction system.

As described above, FMN reductase is inevitable for making the best use of the bacterial luciferase, and when its gene is obtained, it is possible to prepare the present enzyme in a large quantity.

Problem to Be Solved by the Invention

The present inventors have made extensive research, and as a result, have isolated a flavin reductase gene from a luminescent bacterium, Vibrio fischeri (ATCC 7744), and have succeeded in clarifying its primary structure, and further have succeeded in preparing Escherichia coli expressing the gene in a large quantity. Thus, the present invention has been completed.

Namely, in view of the above technical situation, the object of the present invention is to provide a flavin reductase gene of luminescent bacterium, Vibrio fischeri, and a flavin reductase, and the object is further to provide a recombinant vector containing the gene and a bacterium containing the recombinant vector.

SUMMARY OF THE INVENTION

Means for Solving the Problem

The present invention has the following constitutions (1) to (8):

(1) The flavin reductase gene having the following nucleotide sequence:

```
ATG CCN ATH AAY TGY AAR GTN AAR TCN ATH GAR CCN YTN GCN TGY AAY    48
Met Pro Ile Asn Cys Lys Val Lys Ser Ile Glu Pro Leu Ala Cys Asn
 1           5                   10                  15

ACN TTY MGN ATH YTN YTN CAY CCN GAR CAR CCN GTN GCN TTY AAR GCN    96
Thr Phe Arg Ile Leu Leu His Pro Glu Gln Pro Val Ala Phe Lys Ala
             20                  25                  30

GGN CAR TAY YTN ACN GTN GTN ATG GGN GAR AAR GAY AAR MGN CCN TTY   144
Gly Gln Tyr Leu Thr Val Val Met Gly Glu Lys Asp Lys Arg Pro Phe
         35                  40                  45

TCN ATH GCN TCN TCN CCN TGY MGN CAY GAR GGN GAR ATH GAR YTN CAY   192
Ser Ile Ala Ser Ser Pro Cys Arg His Glu Gly Glu Ile Glu Leu His
         50                  55                  60

ATH GGN GCN GCN GAR CAY AAY GCN TAY GCN GGN GAR GTN GTN GAR TCN   240
Ile Gly Ala Ala Glu His Asn Ala Tyr Ala Gly Glu Val Val Glu Ser
 65                  70                  75                  80

ATG AAR TCN GCN YTN GAR ACN GGN GGN GAY ATH YTN ATH GAY GCN CCN   288
Met Lys Ser Ala Leu Glu Thr Gly Gly Asp Ile Leu Ile Asp Ala Pro
                 85                  90                  95

CAY GGN GAR GCN TGG ATH MGN GAR GAY TCN GAY MGN TCN ATG YTN YTN   336
His Gly Glu Ala Trp Ile Arg Glu Asp Ser Asp Arg Ser Met Leu Leu
            100                 105                 110
```

```
ATH GCN GGN GGN ACN GGN TTY TCN TAY GTN MGN TCN ATH YTN GAY CAY   384
Ile Ala Gly Gly Thr Gly Phe Ser Tyr Val Arg Ser Ile Leu Asp His
            115                 120             125

TGY ATH TCN CAR CAR ATH CAR AAR CCN ATH TAY YTN TAY TGG GGN GGN   432
Cys Ile Ser Gln Gln Ile Gln Lys Pro Ile Tyr Leu Tyr Trp Gly Gly
    130                 135                 140

MGN GAY GAR TGY CAR YTN TAY GCN AAR GCN GAR YTN GAR TCN ATH GCN   480
Arg Asp Glu Cys Gln Leu Tyr Ala Lys Ala Glu Leu Glu Ser Ile Ala
145                 150                 155                 160

CAR GCN CAY TCN CAY ATH ACN TTY GTN CCN GTN GTN GAR AAR TCN GAR   528
Gln Ala His Ser His Ile Thr Phe Val Pro Val Val Glu Lys Ser Glu
                165                 170                 175

GGN TGG ACN GGN AAR ACN GGN AAY GTN YTN GAR GCN GTN AAR GCN GAY   576
Gly Trp Thr Gly Lys Thr Gly Asn Val Leu Glu Ala Val Lys Ala Asp
            180                 185                 190

TTY AAY TCN YTN GCN GAY ATG GAY ATH TAY ATH GCN GGN MGN TTY GAR   624
Phe Asn Ser Leu Ala Asp Met Asp Ile Tyr Ile Ala Gly Arg Phe Glu
        195                 200                 205

ATG GCN GGN GCN GCN MGN GAR CAR TTY ACN ACN GAR AAR CAR GCN AAR   672
Met Ala Gly Ala Ala Arg Glu Gln Phe Thr Thr Glu Lys Gln Ala Lys
    210                 215                 220

AAR GAR CAR YTN TTY GGN GAY GCN TTY GCN TTY ATH TRR               711
Lys Glu Gln Leu Phe Gly Asp Ala Phe Ala Phe Ile ***
225                 230                 235
``` wherein the sequence is displayed in numbered triplets of capital letters, which numbers proceed sequentially from left to right and from the 5' terminus to the 3' terminus; the sequence of capital letters represent the purine and pyrimidine bases of the nucleotide sequence, as follows:

A is adenine; G is guanine; C is cytosine; T is thymine; R is A or G; Y is T or C; N is A, T, C, or G; H is A, C, or T; and M is A or C;

wherein triplet number 237 thereof is TAA or TAG or TGA; and wherein further: for triplets numbered 13, 21, 22, 36, 63, 85, 92, 111, 112, 126, 140, 150, 156, 186, 196, and 228, if the 3' nucleotide of a triplet is A or G, then the 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G;

for triplets numbered 19, 46, 56, 103, 108, 123, 145, 206, and 214, if the 3' nucleotide of a triplet is T or C, then the 5' nucleotide of said triplet is A or C, or if the 3' nucleotide of a triplet is T or C, then the 5' nucleotide of said triplet is C; and if the 5' nucleotide of a triplet is G, then the 3' nucleotide of said triplet is A, T, C, or G, or if the 5' nucleotide of a triplet is A, then the 3' nucleotide of said triplet is A or G.

(2) The flavin reductase gene according to item (1), which comprises the following sequence:

```
ATG CCA ATC AAT TGC AAA GTA AAG TCT ATC GAG CCA TTG GCT TGT AAT   48
Met Pro Ile Asn Cys Lys Val Lys Ser Ile Glu Pro Leu Ala Cys Asn
1               5               10              15

ACT TTT CGA ATT TTA CTT CAC CCA GAA CAG CCT GTT GCT TTT AAA GCA   96
Thr Phe Arg Ile Leu Leu His Pro Glu Gln Pro Val Ala Phe Lys Ala
            20              25              30

GGC CAA TAC CTA ACG GTT GTT ATG GGT GAA AAA GAC AAA CGC CCA TTC   144
Gly Gln Tyr Leu Thr Val Val Met Gly Glu Lys Asp Lys Arg Pro Phe
        35              40              45

TCA ATC GCA AGT AGT CCT TGT CGC CAC GAA GGT GAA ATT GAG TTA CAT   192
Ser Ile Ala Ser Ser Pro Cys Arg His Glu Gly Glu Ile Glu Leu His
    50              55              60

ATT GGT GCC GCA GAG CAC AAT GCT TAT GCC GGA GAA GTG GTT GAA TCA   240
Ile Gly Ala Ala Glu His Asn Ala Tyr Ala Gly Glu Val Val Glu Ser
65              70              75              80

ATG AAA TCG GCA CTA GAA ACG GGT GGT GAT ATT TTA ATT GAT GCG CCT   288
Met Lys Ser Ala Leu Glu Thr Gly Gly Asp Ile Leu Ile Asp Ala Pro
            85              90              95

CAT GGT GAA GCG TGG ATC CGT GAA GAC AGC GAT CGT TCA ATG TTA TTG   336
His Gly Glu Ala Trp Ile Arg Glu Asp Ser Asp Arg Ser Met Leu Leu
        100             105             110
```

-continued

```
ATT GCT GGC GGT ACA GGT TTT AGT TAC GTA CGT TCA ATT CTT GAT CAC    384
Ile Ala Gly Gly Thr Gly Phe Ser Tyr Val Arg Ser Ile Leu Asp His
            115                 120                 125

TGT ATT AGC CAA CAG ATT CAA AAA CCA ATT TAC CTA TAC TGG GGT GGT    432
Cys Ile Ser Gln Gln Ile Gln Lys Pro Ile Tyr Leu Tyr Trp Gly Gly
        130                 135                 140

CGT GAT GAA TGC CAA CTG TAT GCA AAA GCA GAA TTA GAG AGC ATT GCT    480
Arg Asp Glu Cys Gln Leu Tyr Ala Lys Ala Glu Leu Glu Ser Ile Ala
145                 150                 155                 160

CAA GCG CAT AGC CAT ATT ACG TTT GTG CCA GTG GTT GAG AAA AGT GAA    528
Gln Ala His Ser His Ile Thr Phe Val Pro Val Val Glu Lys Ser Glu
                165                 170                 175

GGC TGG ACA GGT AAA ACG GGT AAT GTG TTA GAA GCG GTA AAA GCC GAT    576
Gly Trp Thr Gly Lys Thr Gly Asn Val Leu Glu Ala Val Lys Ala Asp
            180                 185                 190

TTT AAC TCA CTA GCA GAT ATG GAT ATT TAC ATC GCA GGT CGC TTT GAA    624
Phe Asn Ser Leu Ala Asp Met Asp Ile Tyr Ile Ala Gly Arg Phe Glu
        195                 200                 205

ATG GCT GGT GCA GCA CGT GAG CAG TTC ACC ACT GAA AAA CAA GCG AAG    672
Met Ala Gly Ala Ala Arg Glu Gln Phe Thr Thr Glu Lys Gln Ala Lys
    210                 215                 220

AAA GAG CAG CTG TTT GGT GAT GCA TTC GCA TTT ATC TAA  (SEQ ID NO:3)    711
Lys Glu Gln Leu Phe Gly Asp Ala Phe Ala Phe Ile ***
225                 230                 235
```

(3) The flavin reductase gene comprising the following nucleotide sequence:

```
  C TCG AGG CGG GAA TTA ATT ATC CAA ACC GAT GCC AAG TCG GCG CAT    46

GTG CTA TGT GCT TAT GCA AAA AAT TAG AGG GTG AAA TTG AAT ACG ATT    94

TAG AGC CTC TTC TTA CCG ATA AAG AAC AAC AAG AAG GGT GGG TAT TTG   142

CGT GTC AGG CAA CAG CAA AAA GTG ATT TAG TGC TGT TGT TAG AAT AAA   190

TCC TCC CCG TAT AAT TAG AGT TTA ATG CTC AAT ACA CAT AAT AAT GAC   238

AGC GTA CAA ATG CCA TAT TAA AAA GGC ATC AGC TGA AAA AGG AAA GTC   286

ATG CCA ATC AAT TGC AAA GTA AAG TCT ATC GAG CCA TTG GCT TGT AAT   334
Met Pro Ile Asn Cys Lys Val Lys Ser Ile Glu Pro Leu Ala Cys Asn
  1               5                  10                  15

ACT TTT CGA ATT TTA CTT CAC CCA GAA CAG CCT GTT GCT TTT AAA GCA   382
Thr Phe Arg Ile Leu Leu His Pro Glu Gln Pro Val Ala Phe Lys Ala
          20                  25                  30

GGC CAA TAC CTA ACG GTT GTT ATG GGT GAA AAA GAC AAA CGC CCA TTC   430
Gly Gln Tyr Leu Thr Val Val Met Gly Glu Lys Asp Lys Arg Pro Phe
      35                  40                  45

TCA ATC GCA AGT AGT CCT TGT CGC CAC GAA GGT GAA ATT GAG TTA CAT   478
Ser Ile Ala Ser Ser Pro Cys Arg His Glu Gly Glu Ile Glu Leu His
  50                  55                  60

ATT GGT GCC GCA GAG CAC AAT GCT TAT GCC GGA GAA GTG GTT GAA TCA   526
Ile Gly Ala Ala Glu His Asn Ala Tyr Ala Gly Glu Val Val Glu Ser
65                  70                  75                  80

ATG AAA TCG GCA CTA GAA ACG GGT GGT GAT ATT TTA ATT GAT GCG CCT   574
Met Lys Ser Ala Leu Glu Thr Gly Gly Asp Ile Leu Ile Asp Ala Pro
          85                  90                  95

CAT GGT GAA GCG TGG ATC CGT GAA GAC AGC GAT CGT TCA ATG TTA TTG   622
His Gly Glu Ala Trp Ile Arg Glu Asp Ser Asp Arg Ser Met Leu Leu
              100                 105                 110
```

```
                                                           -continued
ATT GCT GGC GGT ACA GGT TTT AGT TAC GTA CTG TCA ATT CTT GAT CAC    670
Ile Ala Gly Gly Thr Gly Phe Ser Tyr Val Arg Ser Ile Leu Asp His
        115                 120                 125

TGT ATT AGC CAA CAG ATT CAA AAA CCA ATT TAC CTA TAC TGG GGT GGT    718
Cys Ile Ser Gln Gln Ile Gln Lys Pro Ile Tyr Leu Tyr Trp Gly Gly
    130                 135                 140

CGT GAT GAA TGC CAA CTG TAT GCA AAA GCA GAA TTA GAG AGC ATT GCT    766
Arg Asp Glu Cys Gln Leu Tyr Ala Lys Ala Glu Leu Glu Ser Ile Ala
145                 150                 155                 160

CAA GCG CAT AGC CAT ATT ACG TTT GTG CCA GTG GTT GAG AAA AGT GAA    814
Gln Ala His Ser His Ile Thr Phe Val Pro Val Val Glu Lys Ser Glu
            165                 170                 175

GGC TGG ACA GGT AAA ACG GGT AAT GTG TTA GAA GCG GTA AAA GCC GAT    862
Gly Trp Thr Gly Lys Thr Gly Asn Val Leu Glu Ala Val Lys Ala Asp
        180                 185                 190

TTT AAC TCA CTA GCA GAT ATG GAT ATT TAC ATC GCA GGT CGC TTT GAA    910
Phe Asn Ser Leu Ala Asp Met Asp Ile Tyr Ile Ala Gly Arg Phe Glu
    195                 200                 205

ATG GCT GGT GCA GCA CGT GAG CAG TTC ACC ACT GAA AAA CAA GCG AAG    958
Met Ala Gly Ala Ala Arg Glu Gln Phe Thr Thr Glu Lys Gln Ala Lys
210                 215                 220

AAA GAG CAG CTG TTT GGT GAT GCA TTC GCA TTT ATC TAA TTT AGA GCA   1006
Lys Glu Gln Leu Phe Gly Asp Ala Phe Ala Phe Ile ***
225                 230                 235

CTA AAA AGA CAA ATA AAA ATG CCA CTC AAT AAT GAG TGG CAT TTT TTT   1054

ATG GAT GTT ATA AAA AAT GAA TTA GCC TTT ATC ATC AAC CAT AGT CAG   1102

TGC TTT ACG AGA AAG ATC T    (SEQ ID NO: 5)                       1121
```

(4) The flavin reductase enzyme having an amino acid sequence comprising:

```
Met Pro Ile Asn Cys Lys Val Lys Ser Ile Glu Pro Leu Ala Cys Asn
1               5                   10                  15

Thr Phe Arg Ile Leu Leu His Pro Glu Gln Pro Val Ala Phe Lys Ala
            20                  25                  30

Gly Gln Tyr Leu Thr Val Val Met Gly Glu Lys Asp Lys Arg Pro Phe
        35                  40                  45

Ser Ile Ala Ser Ser Pro Cys Arg His Glu Gly Glu Ile Glu Leu His
    50                  55                  60

Ile Gly Ala Ala Glu His Asn Ala Tyr Ala Gly Glu Val Val Glu Ser
65                  70                  75                  80

Met Lys Ser Ala Leu Glu Thr Gly Gly Asp Ile Leu Ile Asp Ala Pro
            85                  90                  95

His Gly Glu Ala Trp Ile Arg Glu Asp Ser Asp Arg Ser Met Leu Leu
        100                 105                 110

Ile Ala Gly Gly Thr Gly Phe Ser Tyr Val Arg Ser Ile Leu Asp His
    115                 120                 125

Cys Ile Ser Gln Gln Ile Gln Lys Pro Ile Tyr Leu Tyr Trp Gly Gly
130                 135                 140

Arg Asp Glu Cys Gln Leu Tyr Ala Lys Ala Glu Leu Glu Ser Ile Ala
145                 150                 155                 160

Gln Ala His Ser His Ile Thr Phe Val Pro Val Val Glu Lys Ser Glu
            165                 170                 175

Gly Trp Thr Gly Lys Thr Gly Asn Val Leu Glu Ala Val Lys Ala Asp
        180                 185                 190
```

-continued

Phe Asn Ser Leu Ala Asp Met Asp Ile Tyr Ile Ala Gly Arg Phe Glu
            195             200             205

Met Ala Gly Ala Ala Arg Glu Gln Phe Thr Thr Glu Lys Gln Ala Lys
        210             215             220

Lys Glu Gln Leu Phe Gly Asp Ala Phe Ala Phe Ile *** (SEQ ID NO: 5)
225             230             235

(5) The recombinant vector comprising SEQ ID NO:1, as set forth in item (1).

(6) The recombinant vector according to item (5), having a gene having the nucleotide sequence SEQ ID NO:1 of item (1) inserted into a plasmid vector.

(7) The bacterium containing a recombinant vector containing SEQ ID NO:1 of item (1).

(8) The process for producing an enzyme containing an amino acid sequence expressed by SEQ ID NO:6 of item (4), which process comprises cultivating a bacterium modified by a recombinant vector containing a DNA expressed by SEQ ID NO:1 of item (1).

BRIEF DESCRIPTION OF THE ACCOMPANYING DRAWINGS

FIG. 1 illustrates amino acid sequences (SEQ ID NO:8 and SEQ ID NO:10) having a flavin reductase preserved therein and synthesized oligonucleotide primers.

FIG. 2 illustrates a restriction enzyme map of the enzyme gene of the present invention and a sequence strategy. The arrow marks each indicate the direction in which the nucleotide sequence has been determined. The part indicated by the box corresponds to the structural gene part of the enzyme.

FIG. 3 illustrates the construction steps of the expression vector pf FRI of the present invention containing a flavin reductase gene of the luminescent bacterium. The white box indicates the coding region of the flavin reductase gene. The dotted lines indicate the vector part of pUC13 and the black box indicates the promoter part of lactose operon of Escherichia coli.

Explanation of the symbols:
lacP: promoter of lactose operon
pUC13: plasmid vector
λVF2: recombinant phage DNA
pVF2: recombinant plasmid
pfFR1: expression plasmid
HpaI; restriction enzyme
SacII: restriction enzyme
SnaBI: restriction enzyme
PacI: restriction enzyme
SacII: restriction enzyme
NspV: restriction enzyme
BglII: restriction enzyme
SalI: restriction enzyme
HindIII: restriction enzyme
XhoI: restriction enzyme

DETAILED DESCRIPTION OF PREFERRED EMBODIMENTS

The constitution and effectiveness of the present invention will be described below.

The enzyme gene of the present invention is characterized by containing a nucleotide chain having a sequence length of 711, expressed by SEQ ID NO:1.

The preferable sequence contains a nucleotide chain expressed by SEQ ID NO:2.

The sequence of DNA having a sequence length of 1221, and expressed by SEQ ID NO:5 can be concretely exemplified.

The kind of the sequence of the gene is Genomic DNA and the gene is isolated from a luminescent bacterium, Vibrio fischeri (ATCC 7744). The sequence codes a protein of a molecular weight of 26067 consisting of 236 amino acids of sequence No. 287 to No. 994 of SEQ ID NO:5, for example.

The enzyme gene product of the present invention has a flavin reducing activity, and for example has an FMN reducing activity.

The enzyme of the present invention is a protein having the amino acid sequence of SEQ ID NO:6, which is derived by translating SEQ ID NO:1, SEQ ID NO:3, and SEQ ID NO:5. The protein consists of 236 amino acids, has a molecular weight of 26067 and exhibits a flavin reducing activity in a luminescent bacterium.

The recombinant vector of the present invention contains a DNA expressed by a nucleotide sequence SEQ ID NO:1. Namely, the recombinant vector of the present invention contains a DNA having a nucleotide sequence expressed by the sequence SEQ ID NO:3 and a functional equivalent thereto. The terms "functional equivalent" refer to a DNA fragment which is usable according to an essentially same method in order to obtain an essentially same result, in the production of an enzyme having an FMN reducing activity of a luminescent bacterium by means of an adequate host.

Namely, the DNA fragment refers to a DNA fragment which can code a protein having the same amino acid sequence even when the nucleotide sequence is different, or a DNA fragment which can code a protein having an FMN reducing activity, although there is a certain difference of amino acid sequence accompanying a certain difference of nucleotide sequence. Concretely, it refers to the nucleotide sequence of the sequence SEQ ID NO:1 or the nucleotide sequence of the sequence SEQ ID NO:1 obtained by site-directed mutagenesis.

For example, it refers to the recombinant vector having the DNA fragment containing the nucleotide sequence inserted into a plasmid vector. As such a vector, pUC (C. Yanisch-Perron, J. Vieira & J. Messing, Gene, 33, 110–115 [1985]), pIN III (Y. Masui, J. Coleman, M. Inouye, Experimental Manipulation of Gene Expression (ed. M. Inouye), p. 15, Academic Press [1983], etc. are usable.

Figure 3:
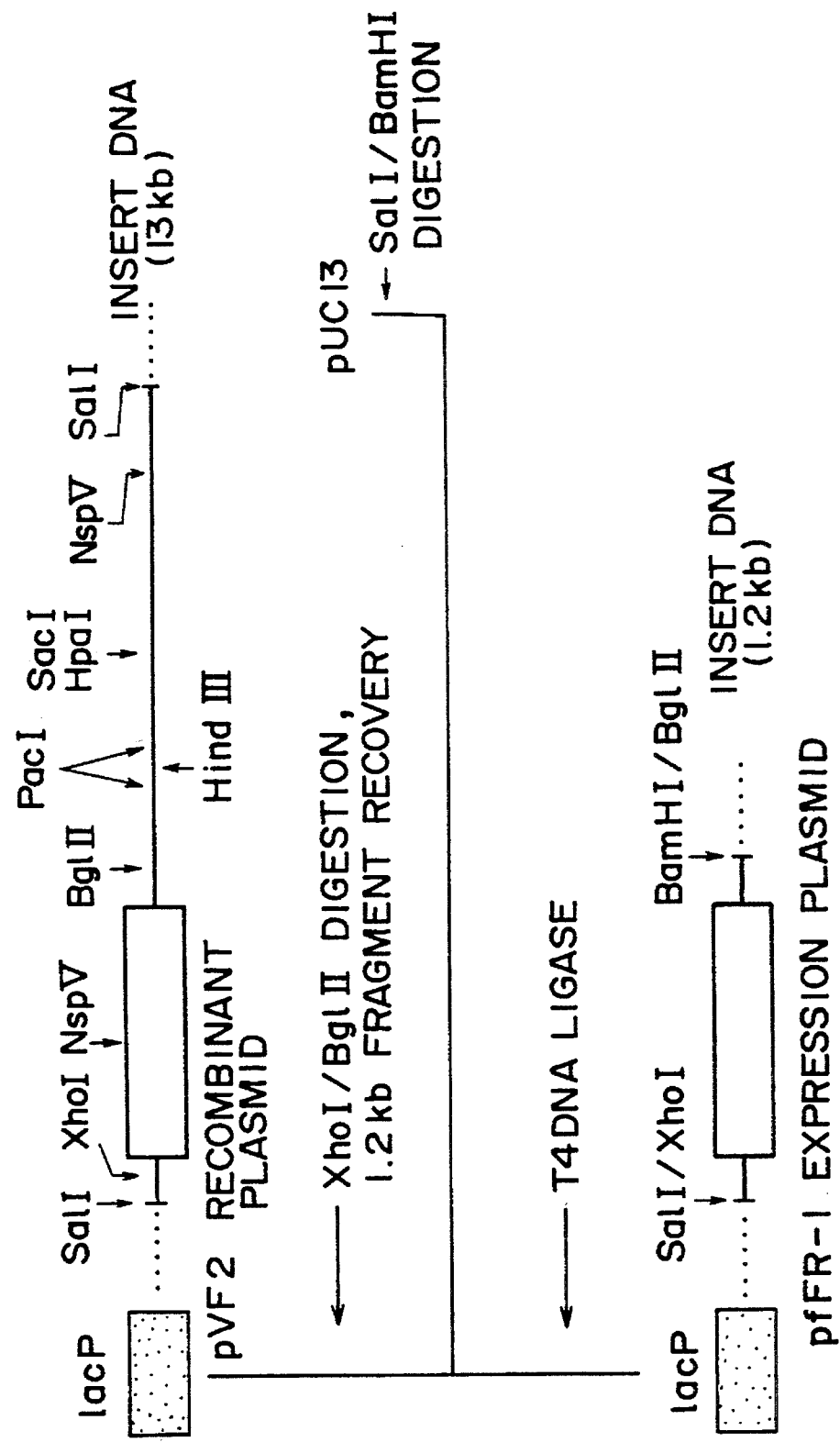

FIG. 3 illustrates the construction steps of the recombinant vector (expression vector). Namely, SalI fragment of about 13 kb as an insert from phage DNA λAVF2 having a reductase gene is inserted into the cleavage site of SalI of pUC13, to obtain a plasmid pVF2, followed by digesting the pVF2 plasmid DNA with XhoI and BglII, recovering the 1.2 kb fragment, and again ligating it to SalI-BamHI cleavage site, to prepare an expression vector pfFR1. As a result, pfFR1 has a flavin reductase gene arranged under the rule of the lac promoter, to thereby express the flavin reductase gene.

The bacterium of the present invention includes a +recombinant DNA containing the nucleotide sequence expressed by the sequence SEQ ID NO:1. The bacterium of the present invention is characterized by producing a protein having a flavin reducing activity.

The production process of the enzyme of the present invention consists in cultivating a bacterium modified by a recombinant vector (expression vector) containing the DNA having a nucleotide sequence expressed by sequence SEQ ID NO:1 to produce a protein containing an amino acid sequence expressed by the sequence SEQ ID NO:6. As the bacterium, Escherichia coli, Bacillus subtilis, etc. are exemplified, and as the medium, LB medium, YT medium, etc. are enumerated.

The procedures of isolating the gene and identifying it, important in the present invention will be described by way of Examples.

EXAMPLE 1

Isolation of a flavin reductase gene (fre) of Vibrio fischeri:

A luminescent bacterium, Vibrio fischeri (ATCC 7744), was cultivated with shaking in a medium of Photobacterium at 26° C. overnight, followed by centrifugal separation at 10,000 rpm, to collect the bacteria, and suspending the bacterial cells in Tris.HCl-EDTA buffer (hereinafter referred to as TE buffer).

The resulting suspension was treated with lyzozyme at 37° C. for one hour, followed by adding sodium dodecylsulfate (hereinafter abbreviated to SDS), subjecting the mixture to proteinase K treatment at 50° C. for 3 hours, three times carrying out phenol treatment, precipitating with ethanol, drying, dissolving in TE buffer, again subjecting to proteinase K treatment, three times treating with phenol, precipitating with ethanol and recovering genome DNA.

Figures 1, 2:
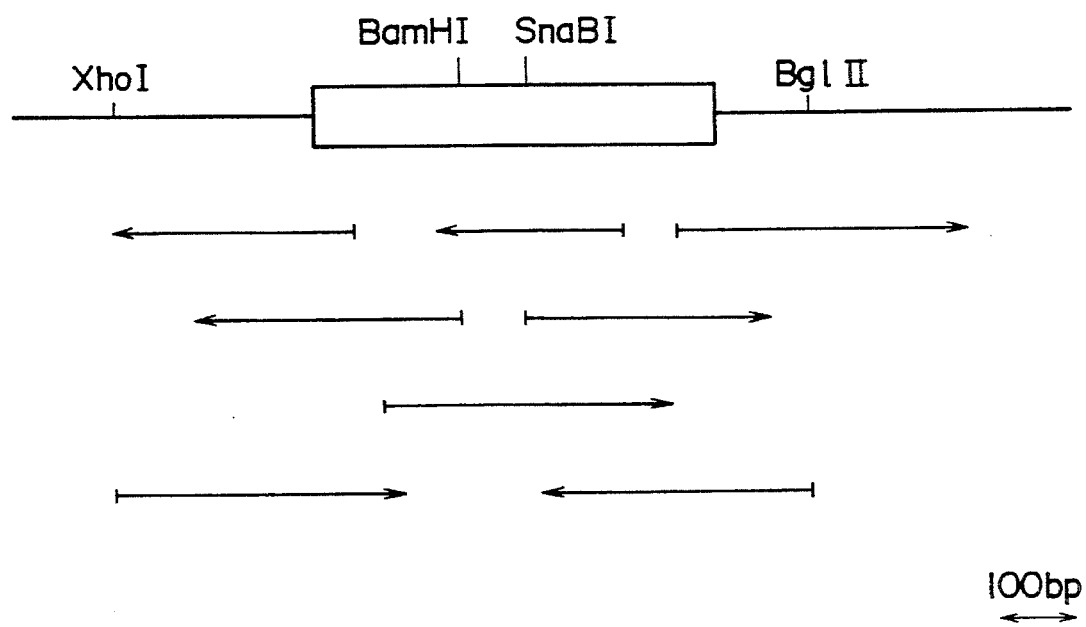

Using synthesized oligonucleotide primers FRE3 and FRE4 shown in FIG. 1, which are portions preserved in the coding regions of Escherichia coli and the flavin reductase enzyme gene (fre) of a luminescent bacterium, Xenorhabdus luminescens (ATCC 29999), the fre gene was amplified using Vibrio fischeri as a template, according to PCR method [Saiki, R. K., D. H. Gelfand, S. Stoffel, S. J. Scharf, R. Higuchi, G. T. Horn, K. B. Mullis and H. A. Erlic (1988), Science 239 487] and the DNA fragment 10 was inserted into the cleavage site of Hinc II of pUC 8 plasmid DNA [Hanna, Z., Fregeau, C., Prefontaine, G., Brousseau, R. (1984), Gene, 30 247].

Determination of nucleotide sequence:

The gene was confirmed to be Vibrio fischeri fre gene according to the method of [Hattori, M. & Sasaki, Y. (1986), Anal. Biochem. 152 232]. From this plasmid DNA, DNA fragment of the fre gene portion was cut off with HindIII/ EcoRi, and was used as a probe DNA for screening of fre gene having a complete chain length. The $^{32}$P labeling of the probe DNA was carried out according to the random priming method [Feinberg, A. & Vogelstein, B. (1983), Anal. Biochem. 132 6].

EXAMPLE 2

Preparation of λ phage library of the luminescent bacterium gene:

The luminescent bacterium, Vibrio fischeri (ATCC 7744) was cultivated under shaking in a Photobacterium medium at 26° C. overnight, followed by subjecting the bacterium to centrifugal separation at 10,000 rpm to collect the bacterium, suspending the bacterial cells in Tris HCl.EDTA buffer (hereinafter referred to as TE buffer), treating the suspension with lyzozyme at 37° C. for one hour, adding sodium dodecylsulfate (hereinafter abbreviated to SDS), subjecting the mixture to protainase K treatment at 50° C. for 3 hours, three times carrying out phenol treatment, precipitating with ethanol, drying, dissolving in TE buffer, again subjecting to proteinase K treatment, three times treating with phenol and precipitating with ethanol, to recover genome DNA.

A restriction enzyme, Sau3AI of 10 units, was reacted with the genome DNA (50 µg) at 37° C., followed by dispersing each portion of the reaction product at the respective reaction times of 5, 10, 20, 30, 45, 60, 90 and 120 minutes, adding EDTA (ethylenediaminetetracetic acid) to terminate the reaction, and subjecting the respective portions to agarose gel electrophoresis to confirm the degree of the partial decomposition of the genome DNA, combining together the reaction solutions of the respective times into one solution, and precipitating with ethanol to recover the precipitate.

The precipitate was dissolved in a small quantity of TE buffer, followed by subjecting the solution to agarose electrophoresis, recovering a fraction of 9 to 23 kilobases (Kb) by means of an electric elution procedure, electrophoretically eluting the DNA of the 9 to 23 Kbs fraction from an agarose gel containing the fraction of 9 to 23 Kbs into a dialysis tube, three times treating with phenol, precipitating with ethanol, and dissolving the precipitate in a TE buffer so as to give about 200 ng/µl.

The DNA of the above fraction of 9 to 23 Kbs was subjected to a ligating reaction with T4 DNA ligase at 16° C. overnight, to EMBL3 phage DNA cleaved by a restriction enzyme BamHI in advance and treated by an alkaline phosphotase. The ligase reaction solution was mixed with a packaging extraction solution, followed by reacting the mixture at 22° C. for 2 hours to prepare a recombinant phage. This phage was made a gene library.

EXAMPLE 3

Isolation of a flavin reductase gene having a complete long chain:

The titer of the gene library prepared in Example 2 was measured, followed by scattering the gene library described above so that 10,000 phages per one plate could form plaques, cultivating at 37° C. overnight, allowing the resulting culture to stand at 4° C. for 2 hours, and transferring phages to two nylon membrane filters against the respective plates.

The filter was denatured, followed by neutralization and then ultraviolet-rays irradiation. Further, it was placed in a hybridization solution {20 ml of 6×SET buffer [20×SET buffer: NaCl (3 M), Tris-HCl (pH 8.0) (0.6M) and EDTA (0.04M)], 10×Denhardt's solution (calf serum albumin, polyvinyl pyrrolidone, and Ficoll, each 0.2% solution), 0.1% SDS and salmon sperm DNA (heat-denatured, 50 µg/ml)}, followed by keeping the temperature at 68° C. for one hour.

Further, the solution was replaced, followed by keeping the temperature at 68° C. for one hour, adding a probe of $^{32}$P-labeled Vbrio fischeri fre, hybridizing at 65° C. overnight, discarding the solution, washing the filter with a 2×SET buffer, shaking with 0.2×SET buffer at 65° C. for 20 minutes, twice repeating this procedure, air-drying; subjecting to autoradiography, overlaying the filter on a developed X-ray film, and photographing the position of ink marker on the film.

A positive phage (clone) whose signal was identified to overlie on two films made from one plate, was obtained from about 1,000 recombinant phages. This clone was named λVF2. This insert DNA was inserted into the SalI site of pUC13 plasmid.

Using a synthetic oligonucleotide primer (20 mer) prepared based upon the nucleotide sequence of PCR clone, and using the above plasmid DNA as a template, the nucleotide sequence was determined according to the dideoxy method (Hattori, M. & Sasaki, Y. (1986), Anal. Biochem. 152, 232).

Further, a synthetic primer was newly prepared based upon the nucleotide sequence, and its nucleotide sequence was determined in the same manner. FIG. 2 illustrates its restriction map and the strategy of the sequence determination. The determined nucleotide sequence was as shown in the sequence SEQ ID NO:3, and it was considered that the sequence had a length of 1221 bp and coded a protein consisting of 236 amino acids of nucleotide Nos. 287 to 994 and having a molecular weight of 26067.

EXAMPLE 4

Construction of expression vector of flavin reductase gene and preparation of its transformed strain (see FIG. 3):

DNA of a recombinant plasmid pVF2 was digested with XhoI and BglII, followed by recovering a fragment of 1.2 Kb, subjecting the fragment to a ligation reaction to the SalI/Bam$^{HI}$ site of plasmid pUC13, with T4 DNA ligase transforming a portion of the reaction solution into Escherichia coli D1210 strain, preparing a plasmid DNA from the transformed strain and choosing an insert DNA of 1.2 Kb.

The plasmid was named pfFR1. This pfFR1 was in the form wherein a flavin reductase gene was arranged under the rule of the promoter of lactose operon (lac) and was constructed so as to express the flavin reductase.

EXAMPLE 5

Preparation of flavin reductase and measurement of its activity:

A solution (0.25 ml) obtained by cultivating the above transformed strain overnight was inoculated in an LB liquid medium (10 ml) containing ampicillin (0.1 mg/ml), followed by cultivating under shaking at 37° C. for 2 hours, adding isopropyl-β-D(—)-thiogalactopyranoside (hereinafter abbreviated to IPTG) so as to give a final concentration of 1 mM and further cultivating for 3 hours.

The resulting culture solution (3.0 ml) subjected to IPTG derivation treatment was subjected to centrifugal separation at 10,000 rpm, followed by removing the supernatant, suspending the resulting bacterial cells in a buffer solution (0.75 ml) of 50 mM potassium phosphate containing 1 mM dithiothreitol, subjecting the suspension to ultrasonic crushing and subjecting to centrifugal separation at 4° C. for 30 minutes, to make the supernatant a cell extraction liquid. The enzymatic flavin reducing activity of the cell extraction liquid was measured. The results are shown in Table 1.

TABLE 1

| | Kind of bacterium | Activity of flavin reductase (nmol/min/mg protein) | | |
|---|---|---|---|---|
| | | FMN | FAD | Riboflavin |
| NADH | pfFR1/D1210 | 149 | 59 | 138 |
| | pUC13/D1210 | 27 | 41 | 29 |
| NADPH | pfFR1/D1210 | 15 | 6 | 108 |
| | pUC13/D1210 | 4 | 6 | 19 |

Flavin reductase activity Was measured according to the method of Jablonski, E. & DeLuca, M. (1977), Biochemistry, 16, 2932. The protein concentration was determined using a protein assay kit made by Bio-Rad Co., Ltd., and according to dye-binding method (Bradford., M. M. (1976), Anal. Biochem. 72, 248–254).

As seen from the results of Table 1, the values of the reductase activities of FMN and riboflavin of pfFR1 were higher by a number of one cipher than those of pUC13. This gene was confirmed to code the flavin reductase.

Effectiveness of the Invention:

The enzyme gene of the present invention was isolated as a gene of enzyme having FMN reducing activity of a luminescent bacterium, Vibrio fischeri By employing a suitable host such as Escherichia coli, it is possible to prepare a large quantity of the enzyme protein from the Escherichia coli.

By introducing its expression vector into a suitable host such as Escherichia coli, it is possible to prepare an organism or microorganism expressing an enzyme having an FMN reducing activity of the luminescent bacterium, in a large quantity, and further, by extracting the enzyme from the organism having introduced the gene, it is possible to prepare the reductase in a large quantity.

Due to the above-mentioned functions, the reductase amplifies the luminescent reaction of the bacterial luciferase, can be applied to a number of measurement methods, and is useful for example as diagnostic medicine or inspection medicine.

What we claim is:

1. A flavin reductase gene having the nucleotide sequence of SEQ ID NO:1, wherein the sequence is displayed in numbered triplets of capital letters, which numbers proceed sequentially from left to right and from the 5' terminus to the 3' terminus; the sequence of capital letters represent the purine and pyrimidine bases of the nucleotide sequence, as follows:

A is adenine; G is guanine; C is cytosine; T is thymine; R is A or G; Y is T or C; N is A, T, C, or G; H is A, C, or T; and M is A or C;

wherein triplet number 237 thereof is TAA or TAG or TGA; and wherein further: for triplets numbered 13, 21, 22, 36, 63, 85, 92, 111, 112, 126, 140, 150, 156, 186, 196, and 228, if the 3' nucleotide of a triplet is A or G, then the 5' nucleotide of said triplet is T or C, or if the 3' nucleotide of a triplet is T or C, then the 5' nucleotide of said triplet is C; and if the 5' nucleotide of a triplet is C, then the 3' nucleotide of said triplet is A, T, C, or G, or if the 5' nucleotide of a triplet is T, then the 3' nucleotide of said triplet is A or G;

for triplets numbered 19, 46, 56, 103, 108, 123, 145, 206, and 214, if the 3' nucleotide of a triplet is T or C, then the 5' nucleotide of said triplet is A or C, or if the 3' nucleotide of a triplet is T or C, then the 5' nucleotide of said triplet is C; and if the 5' nucleotide of a triplet is G, then the 3' nucleotide of said triplet is A, T, C, or G, or if the 5' nucleotide of a triplet is A, then the 3' nucleotide of said triplet is A or G.

2. The flavin reductase gene according to claim 1, wherein said gene has the nucleotide sequence of SEQ ID NO:3.

3. A flavin reductase gene having the nucleotide sequence of SEQ ID NO:5.

4. A flavin reductase enzyme having the amino acid sequence of SEQ ID NO:6.

5. A recombinant vector comprising the nucleotide sequence of SEQ ID NO:1, as set forth in claim 1.

6. The recombinant vector according to claim 5, wherein said SEQ ID NO:1 is inserted into a plasmid vector.

7. A bacterium having a recombinant vector comprising the flavin reductase gene according to claim 1.

8. A process for producing an enzyme having the amino acid sequence of SEQ ID NO:6, comprising cultivating a bacterium according to claim 7.

* * * * *

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 711 base pairs
        ( B ) TYPE: nucleic acid
        ( C ) STRANDEDNESS: double -continued (D) TOPOLOGY: linear (ii) MOLECULE TYPE: DNA (genomic)

(ix) FEATURE:
  (A) NAME/KEY: CDS
  (B) LOCATION: 1..711

(xi) SEQUENCE DESCRIPTION: SEQ ID NO:1:

| ATG | CCN | ATH | AAY | TGY | AAR | GTN | AAR | TCN | ATH | GAR | CCN | YTN | GCN | TGY | AAY | 48 |
| Met | Pro | Ile | Asn | Cys | Lys | Val | Lys | Ser | Ile | Glu | Pro | Leu | Ala | Cys | Asn | |
| 1 | | | | 5 | | | | | 10 | | | | | 15 | | |

| ACN | TTY | MGN | ATH | YTN | YTN | CAR | CCN | GAR | CAR | CCN | GTN | GCN | TTY | AAR | GCN | 96 |
| Thr | Phe | Arg | Ile | Leu | Leu | His | Pro | Glu | Gln | Pro | Val | Ala | Phe | Lys | Ala | |
| | | | 20 | | | | | 25 | | | | | 30 | | | |

| GGN | CAR | TAK | YTN | ACN | GTN | GTN | ATG | GGN | GAR | AAR | GAY | AAR | MGN | CCN | TTY | 144 |
| Gly | Gln | Tyr | Leu | Thr | Val | Val | Met | Gly | Glu | Lys | Asp | Lys | Arg | Pro | Phe | |
| | | 35 | | | | | 40 | | | | | 45 | | | | |

| TCN | ATH | GCN | TCN | TCN | CCN | TGY | MGN | CAR | GAR | GGN | GAR | ATH | GAR | YTN | CAR | 192 |
| Ser | Ile | Ala | Ser | Ser | Pro | Cys | Arg | His | Glu | Gly | Glu | Ile | Glu | Leu | His | |
| | 50 | | | | | 55 | | | | | 60 | | | | | |

| ATH | GGN | GCN | GCN | GAR | CAR | AAY | GCN | TAK | GCN | GGN | GAR | GTN | GTN | GAR | TCN | 240 |
| Ile | Gly | Ala | Ala | Glu | His | Asn | Ala | Tyr | Ala | Gly | Glu | Val | Val | Glu | Ser | |
| 65 | | | | | 70 | | | | | 75 | | | | | 80 | |

| ATG | AAR | TCN | GCN | YTN | GAR | ACN | GGN | GGN | GAY | ATH | YTN | ATH | GAY | GCN | CCN | 288 |
| Met | Lys | Ser | Ala | Leu | Glu | Thr | Gly | Gly | Asp | Ile | Leu | Ile | Asp | Ala | Pro | |
| | | | | 85 | | | | | 90 | | | | | 95 | | |

| CAR | GGN | GAR | GCN | TGG | ATH | MGN | GAR | GAY | TCN | GAY | MGN | TCN | ATG | YTN | YTN | 336 |
| His | Gly | Glu | Ala | Trp | Ile | Arg | Glu | Asp | Ser | Asp | Arg | Ser | Met | Leu | Leu | |
| | | | 100 | | | | | 105 | | | | | 110 | | | |

| ATH | GCN | GGN | GGN | ACN | GGN | TTY | TCN | TAK | GTN | MGN | TCN | ATH | YTN | GAY | CAR | 384 |
| Ile | Ala | Gly | Gly | Thr | Gly | Phe | Ser | Tyr | Val | Arg | Ser | Ile | Leu | Asp | His | |
| | | 115 | | | | | 120 | | | | | 125 | | | | |

| TGY | ATH | TCN | CAR | CAR | ATH | CAR | AAR | CCN | ATH | TAK | YTN | TAK | TGG | GGN | GGN | 432 |
| Cys | Ile | Ser | Gln | Gln | Ile | Gln | Lys | Pro | Ile | Tyr | Leu | Tyr | Trp | Gly | Gly | |
| | 130 | | | | | 135 | | | | | 140 | | | | | |

| MGN | GAY | GAR | TGY | CAR | YTN | TAK | GCN | AAR | GCN | GAR | YTN | GAR | TCN | ATH | GCN | 480 |
| Arg | Asp | Glu | Cys | Gln | Leu | Tyr | Ala | Lys | Ala | Glu | Leu | Glu | Ser | Ile | Ala | |
| 145 | | | | | 150 | | | | | 155 | | | | | 160 | |

| CAR | GCN | CAR | TCN | CAR | ATH | ACN | TTY | GTN | CCN | GTN | GTN | GAR | AAR | TCN | GAR | 528 |
| Gln | Ala | His | Ser | His | Ile | Thr | Phe | Val | Pro | Val | Val | Glu | Lys | Ser | Glu | |
| | | | | 165 | | | | | 170 | | | | | 175 | | |

| GGN | TGG | ACN | GGN | AAR | ACN | GGN | AAY | GTN | YTN | GAR | GCN | GTN | AAR | GCN | GAY | 576 |
| Gly | Trp | Thr | Gly | Lys | Thr | Gly | Asn | Val | Leu | Glu | Ala | Val | Lys | Ala | Asp | |
| | | | 180 | | | | | 185 | | | | | 190 | | | |

| TTY | AAY | TCN | YTN | GCN | GAY | ATG | GAY | ATH | TAK | ATH | GCN | GGN | MGN | TTY | GAR | 624 |
| Phe | Asn | Ser | Leu | Ala | Asp | Met | Asp | Ile | Tyr | Ile | Ala | Gly | Arg | Phe | Glu | |
| | | 195 | | | | | 200 | | | | | 205 | | | | |

| ATG | GCN | GGN | GCN | GCN | MGN | GAR | CAR | TTY | ACN | ACN | GAR | AAR | CAR | GCN | AAR | 672 |
| Met | Ala | Gly | Ala | Ala | Arg | Glu | Gln | Phe | Thr | Thr | Glu | Lys | Gln | Ala | Lys | |
| 210 | | | | | 215 | | | | | 220 | | | | | | |

| AAR | GAR | CAR | YTN | TTY | GGN | GAY | GCN | TTY | GCN | TTY | ATH | TRR | | | | 711 |
| Lys | Glu | Gln | Leu | Phe | Gly | Asp | Ala | Phe | Ala | Phe | Ile | *** | | | | |
| 225 | | | | | 230 | | | | | 235 | | | | | | |

(2) INFORMATION FOR SEQ ID NO:2:

(i) SEQUENCE CHARACTERISTICS:
    (A) LENGTH: 236 amino acids
    (B) TYPE: amino acid
    (D) TOPOLOGY: linear (ii) MOLECULE TYPE: protein ( x i ) SEQUENCE DESCRIPTION: SEQ ID NO:2:

| Met | Pro | Ile | Asn | Cys | Lys | Val | Lys | Ser | Ile | Glu | Pro | Leu | Ala | Cys | Asn |
|---|---|---|---|---|---|---|---|---|---|---|---|---|---|---|---|
| 1 | | | | 5 | | | | 10 | | | | | | 15 | |

| Thr | Phe | Arg | Ile | Leu | Leu | His | Pro | Glu | Gln | Pro | Val | Ala | Phe | Lys | Ala |
|---|---|---|---|---|---|---|---|---|---|---|---|---|---|---|---|
| | | | 20 | | | | | 25 | | | | | 30 | | |

| Gly | Gln | Tyr | Leu | Thr | Val | Val | Met | Gly | Glu | Lys | Asp | Lys | Arg | Pro | Phe |
|---|---|---|---|---|---|---|---|---|---|---|---|---|---|---|---|
| | | 35 | | | | | 40 | | | | | 45 | | | |

| Ser | Ile | Ala | Ser | Ser | Pro | Cys | Arg | His | Glu | Gly | Glu | Ile | Glu | Leu | His |
|---|---|---|---|---|---|---|---|---|---|---|---|---|---|---|---|
| | 50 | | | | | 55 | | | | | 60 | | | | |

| Ile | Gly | Ala | Ala | Glu | His | Asn | Ala | Tyr | Ala | Gly | Glu | Val | Val | Glu | Ser |
|---|---|---|---|---|---|---|---|---|---|---|---|---|---|---|---|
| 65 | | | | | 70 | | | | | 75 | | | | | 80 |

| Met | Lys | Ser | Ala | Leu | Glu | Thr | Gly | Gly | Asp | Ile | Leu | Ile | Asp | Ala | Pro |
|---|---|---|---|---|---|---|---|---|---|---|---|---|---|---|---|
| | | | | 85 | | | | | 90 | | | | | 95 | |

| His | Gly | Glu | Ala | Trp | Ile | Arg | Glu | Asp | Ser | Asp | Arg | Ser | Met | Leu | Leu |
|---|---|---|---|---|---|---|---|---|---|---|---|---|---|---|---|
| | | | 100 | | | | | 105 | | | | | 110 | | |

| Ile | Ala | Gly | Gly | Thr | Gly | Phe | Ser | Tyr | Val | Arg | Ser | Ile | Leu | Asp | His |
|---|---|---|---|---|---|---|---|---|---|---|---|---|---|---|---|
| | | 115 | | | | | 120 | | | | | 125 | | | |

| Cys | Ile | Ser | Gln | Gln | Ile | Gln | Lys | Pro | Ile | Tyr | Leu | Tyr | Trp | Gly | Gly |
|---|---|---|---|---|---|---|---|---|---|---|---|---|---|---|---|
| | 130 | | | | | 135 | | | | | 140 | | | | |

| Arg | Asp | Glu | Cys | Gln | Leu | Tyr | Ala | Lys | Ala | Glu | Leu | Glu | Ser | Ile | Ala |
|---|---|---|---|---|---|---|---|---|---|---|---|---|---|---|---|
| 145 | | | | | 150 | | | | | 155 | | | | | 160 |

| Gln | Ala | His | Ser | His | Ile | Thr | Phe | Val | Pro | Val | Val | Glu | Lys | Ser | Glu |
|---|---|---|---|---|---|---|---|---|---|---|---|---|---|---|---|
| | | | | 165 | | | | | 170 | | | | | 175 | |

| Gly | Trp | Thr | Gly | Lys | Thr | Gly | Asn | Val | Leu | Glu | Ala | Val | Lys | Ala | Asp |
|---|---|---|---|---|---|---|---|---|---|---|---|---|---|---|---|
| | | | 180 | | | | | 185 | | | | | 190 | | |

| Phe | Asn | Ser | Leu | Ala | Asp | Met | Asp | Ile | Tyr | Ile | Ala | Gly | Arg | Phe | Glu |
|---|---|---|---|---|---|---|---|---|---|---|---|---|---|---|---|
| | | 195 | | | | | 200 | | | | | 205 | | | |

| Met | Ala | Gly | Ala | Ala | Arg | Glu | Gln | Phe | Thr | Thr | Glu | Lys | Gln | Ala | Lys |
|---|---|---|---|---|---|---|---|---|---|---|---|---|---|---|---|
| | 210 | | | | | 215 | | | | | 220 | | | | |

| Lys | Glu | Gln | Leu | Phe | Gly | Asp | Ala | Phe | Ala | Phe | Ile |
|---|---|---|---|---|---|---|---|---|---|---|---|
| 225 | | | | | 230 | | | | | 235 | |

( 2 ) INFORMATION FOR SEQ ID NO:3:

( i ) SEQUENCE CHARACTERISTICS:
        ( A ) LENGTH: 711 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..711

( x i ) SEQUENCE DESCRIPTION: SEQ ID NO:3:

| ATG | CCA | ATC | AAT | TGC | AAA | GTA | AAG | TCT | ATC | GAG | CCA | TTG | GCT | TGT | AAT | 48 |
|---|---|---|---|---|---|---|---|---|---|---|---|---|---|---|---|---|
| Met | Pro | Ile | Asn | Cys | Lys | Val | Lys | Ser | Ile | Glu | Pro | Leu | Ala | Cys | Asn | |
| 1 | | | | 5 | | | | 10 | | | | | | 15 | | |

| ACT | TTT | CGA | ATT | TTA | CTT | CAC | CCA | GAA | CAG | CCT | GTT | GCT | TTT | AAA | GCA | 96 |
|---|---|---|---|---|---|---|---|---|---|---|---|---|---|---|---|---|
| Thr | Phe | Arg | Ile | Leu | Leu | His | Pro | Glu | Gln | Pro | Val | Ala | Phe | Lys | Ala | |
| | | | 20 | | | | | 25 | | | | | 30 | | | |

| GGC | CAA | TAC | CTA | ACG | GTT | GTT | ATG | GGT | GAA | AAA | GAC | AAA | CGC | CCA | TTC | 144 |
|---|---|---|---|---|---|---|---|---|---|---|---|---|---|---|---|---|
| Gly | Gln | Tyr | Leu | Thr | Val | Val | Met | Gly | Glu | Lys | Asp | Lys | Arg | Pro | Phe | |
| | | 35 | | | | | 40 | | | | | 45 | | | | |

| TCA | ATC | GCA | AGT | AGT | CCT | TGT | CGC | CAC | GAA | GGT | GAA | ATT | GAG | TTA | CAT | 192 |
|---|---|---|---|---|---|---|---|---|---|---|---|---|---|---|---|---|
| Ser | Ile | Ala | Ser | Ser | Pro | Cys | Arg | His | Glu | Gly | Glu | Ile | Glu | Leu | His | |

|  |  |  |  |  |  |  |  |  |  |  |  |  |  |  |  |  |
|---|---|---|---|---|---|---|---|---|---|---|---|---|---|---|---|---|
|  | 50 |  |  |  |  | 55 |  |  |  |  | 60 |  |  |  |  |  |
| ATT | GGT | GCC | GCA | GAG | CAC | AAT | GCT | TAT | GCC | GGA | GAA | GTG | GTT | GAA | TCA | 240 |
| Ile | Gly | Ala | Ala | Glu | His | Asn | Ala | Tyr | Ala | Gly | Glu | Val | Val | Glu | Ser |  |
| 65 |  |  |  | 70 |  |  |  |  | 75 |  |  |  |  | 80 |  |  |
| ATG | AAA | TCG | GCA | CTA | GAA | ACG | GGT | GGT | GAT | ATT | TTA | ATT | GAT | GCG | CCT | 288 |
| Met | Lys | Ser | Ala | Leu | Glu | Thr | Gly | Gly | Asp | Ile | Leu | Ile | Asp | Ala | Pro |  |
|  |  |  |  | 85 |  |  |  |  | 90 |  |  |  |  | 95 |  |  |
| CAT | GGT | GAA | GCG | TGG | ATC | CGT | GAA | GAC | AGC | GAT | CGT | TCA | ATG | TTA | TTG | 336 |
| His | Gly | Glu | Ala | Trp | Ile | Arg | Glu | Asp | Ser | Asp | Arg | Ser | Met | Leu | Leu |  |
|  |  |  | 100 |  |  |  |  | 105 |  |  |  |  | 110 |  |  |  |
| ATT | GCT | GGC | GGT | ACA | GGT | TTT | AGT | TAC | GTA | CGT | TCA | ATT | CTT | GAT | CAC | 384 |
| Ile | Ala | Gly | Gly | Thr | Gly | Phe | Ser | Tyr | Val | Arg | Ser | Ile | Leu | Asp | His |  |
|  |  | 115 |  |  |  |  | 120 |  |  |  |  | 125 |  |  |  |  |
| TGT | ATT | AGC | CAA | CAG | ATT | CAA | AAA | CCA | ATT | TAC | CTA | TAC | TGG | GGT | GGT | 432 |
| Cys | Ile | Ser | Gln | Gln | Ile | Gln | Lys | Pro | Ile | Tyr | Leu | Tyr | Trp | Gly | Gly |  |
| 130 |  |  |  |  | 135 |  |  |  |  | 140 |  |  |  |  |  |  |
| CGT | GAT | GAA | TGC | CAA | CTG | TAT | GCA | AAA | GCA | GAA | TTA | GAG | AGC | ATT | GCT | 480 |
| Arg | Asp | Glu | Cys | Gln | Leu | Tyr | Ala | Lys | Ala | Glu | Leu | Glu | Ser | Ile | Ala |  |
| 145 |  |  |  |  | 150 |  |  |  |  | 155 |  |  |  |  | 160 |  |
| CAA | GCG | CAT | AGC | CAT | ATT | ACG | TTT | GTG | CCA | GTG | GTT | GAG | AAA | AGT | GAA | 528 |
| Gln | Ala | His | Ser | His | Ile | Thr | Phe | Val | Pro | Val | Val | Glu | Lys | Ser | Glu |  |
|  |  |  |  | 165 |  |  |  |  | 170 |  |  |  |  | 175 |  |  |
| GGC | TGG | ACA | GGT | AAA | ACG | GGT | AAT | GTG | TTA | GAA | GCG | GTA | AAA | GCC | GAT | 576 |
| Gly | Trp | Thr | Gly | Lys | Thr | Gly | Asn | Val | Leu | Glu | Ala | Val | Lys | Ala | Asp |  |
|  |  |  | 180 |  |  |  |  | 185 |  |  |  |  | 190 |  |  |  |
| TTT | AAC | TCA | CTA | GCA | GAT | ATG | GAT | ATT | TAC | ATC | GCA | GGT | CGC | TTT | GAA | 624 |
| Phe | Asn | Ser | Leu | Ala | Asp | Met | Asp | Ile | Tyr | Ile | Ala | Gly | Arg | Phe | Glu |  |
|  |  | 195 |  |  |  |  | 200 |  |  |  |  | 205 |  |  |  |  |
| ATG | GCT | GGT | GCA | GCA | CGT | GAG | CAG | TTC | ACC | ACT | GAA | AAA | CAA | GCG | AAG | 672 |
| Met | Ala | Gly | Ala | Ala | Arg | Glu | Gln | Phe | Thr | Thr | Glu | Lys | Gln | Ala | Lys |  |
|  | 210 |  |  |  |  | 215 |  |  |  |  | 220 |  |  |  |  |  |
| AAA | GAG | CAG | CTG | TTT | GGT | GAT | GCA | TTC | GCA | TTT | ATC | TAA |  |  |  | 711 |
| Lys | Glu | Gln | Leu | Phe | Gly | Asp | Ala | Phe | Ala | Phe | Ile | *** |  |  |  |  |
| 225 |  |  |  |  | 230 |  |  |  |  | 235 |  |  |  |  |  |  |

( 2 ) INFORMATION FOR SEQ ID NO:4:

( i ) SEQUENCE CHARACTERISTICS:
        ( A ) LENGTH: 236 amino acids
        ( B ) TYPE: amino acid
        ( D ) TOPOLOGY: linear ( i i ) MOLECULE TYPE: protein ( i x ) SEQUENCE DESCRIPTION: SEQ ID NO:4:

| Met | Pro | Ile | Asn | Cys | Lys | Val | Lys | Ser | Ile | Glu | Pro | Leu | Ala | Cys | Asn |
|---|---|---|---|---|---|---|---|---|---|---|---|---|---|---|---|
| 1 |  |  |  | 5 |  |  |  |  | 10 |  |  |  |  | 15 |  |
| Thr | Phe | Arg | Ile | Leu | Leu | His | Pro | Glu | Gln | Pro | Val | Ala | Phe | Lys | Ala |
|  |  |  | 20 |  |  |  |  | 25 |  |  |  |  | 30 |  |  |
| Gly | Gln | Tyr | Leu | Thr | Val | Val | Met | Gly | Glu | Lys | Asp | Lys | Arg | Pro | Phe |
|  |  | 35 |  |  |  |  | 40 |  |  |  |  | 45 |  |  |  |
| Ser | Ile | Ala | Ser | Ser | Pro | Cys | Arg | His | Glu | Gly | Glu | Ile | Glu | Leu | His |
|  | 50 |  |  |  |  | 55 |  |  |  |  | 60 |  |  |  |  |
| Ile | Gly | Ala | Ala | Glu | His | Asn | Ala | Tyr | Ala | Gly | Glu | Val | Val | Glu | Ser |
| 65 |  |  |  | 70 |  |  |  |  | 75 |  |  |  |  | 80 |  |
| Met | Lys | Ser | Ala | Leu | Glu | Thr | Gly | Gly | Asp | Ile | Leu | Ile | Asp | Ala | Pro |
|  |  |  |  | 85 |  |  |  |  | 90 |  |  |  |  | 95 |  |
| His | Gly | Glu | Ala | Trp | Ile | Arg | Glu | Asp | Ser | Asp | Arg | Ser | Met | Leu | Leu |
|  |  |  | 100 |  |  |  |  | 105 |  |  |  |  | 110 |  |  |

-continued

```
Ile  Ala  Gly  Gly  Thr  Gly  Phe  Ser  Tyr  Val  Arg  Ser  Ile  Leu  Asp  His
          115                      120                     125

Cys  Ile  Ser  Gln  Gln  Ile  Gln  Lys  Pro  Ile  Tyr  Leu  Tyr  Trp  Gly  Gly
     130                      135                     140

Arg  Asp  Glu  Cys  Glu  Leu  Tyr  Ala  Lys  Ala  Glu  Leu  Glu  Ser  Ile  Ala
145                      150                     155                          160

Gln  Ala  His  Ser  His  Ile  Thr  Phe  Val  Pro  Val  Val  Glu  Lys  Ser  Glu
                    165                     170                     175

Gly  Trp  Thr  Gly  Lys  Thr  Gly  Asn  Val  Leu  Glu  Ala  Val  Lys  Ala  Asp
               180                     185                     190

Phe  Asn  Ser  Leu  Ala  Asp  Met  Asp  Ile  Tyr  Ile  Ala  Gly  Arg  Phe  Glu
          195                      200                     205

Met  Ala  Gly  Ala  Ala  Arg  Glu  Gln  Phe  Thr  Thr  Glu  Lys  Gln  Ala  Lys
     210                      215                     220

Lys  Glu  Gln  Leu  Phe  Gly  Asp  Ala  Phe  Ala  Phe  Ile
225                      230                     235
```

( 2 ) INFORMATION FOR SEQ ID NO:5:

( i ) SEQUENCE CHARACTERISTICS:
        ( A ) LENGTH: 1121 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 287..995

( x i ) SEQUENCE DESCRIPTION: SEQ ID NO:5:

```
CTCGAGGCGG  GAATTAATTA  TCCAAACCGA  TGCCAAGTCG  GCGCATGTGC  TATGTGCTTA       60

TGCAAAAAAT  TAGAGGGTGA  AATTGAATAC  GATTTAGAGC  CTCTTCTTAC  CGATAAAGAA      120

CAACAAGAAG  GGTGGGTATT  TGCGTGTCAG  GCAACAGCAA  AAAGTGATTT  AGTGCTGTTG      180

TTAGAATAAA  TCCTCCCCGT  ATAATTAGAG  TTTAATGCTC  AATACACATA  ATAATGACAG      240

CGTACAAATG  CCATATTAAA  AAGGCATCAG  CTGAAAAAGG  AAAGTC ATG CCA ATC          295
                                                         Met Pro Ile
                                                          1

AAT TGC AAA GTA AAG TCT ATC GAG CCA TTG GCT TGT AAT ACT TTT CGA             343
Asn Cys Lys Val Lys Ser Ile Glu Pro Leu Ala Cys Asn Thr Phe Arg
     5                  10                  15

ATT TTA CTT CAC CCA GAA CAG CCT GTT GCT TTT AAA GCA GGC CAA TAC             391
Ile Leu Leu His Pro Glu Gln Pro Val Ala Phe Lys Ala Gly Gln Tyr
 20                  25                  30                  35

CTA ACG GTT GTT ATG GGT GAA AAA GAC AAA CGC CCA TTC TCA ATC GCA             439
Leu Thr Val Val Met Gly Glu Lys Asp Lys Arg Pro Phe Ser Ile Ala
                     40                  45                  50

AGT AGT CCT TGT CGC CAC GAA GGT GAA ATT GAG TTA CAT ATT GGT GCC             487
Ser Ser Pro Cys Arg His Glu Gly Glu Ile Glu Leu His Ile Gly Ala
             55                  60                  65

GCA GAG CAC AAT GCT TAT GCC GGA GAA GTG GTT GAA TCA ATG AAA TCG             535
Ala Glu His Asn Ala Tyr Ala Gly Glu Val Val Glu Ser Met Lys Ser
         70                  75                  80

GCA CTA GAA ACG GGT GGT GAT ATT TTA ATT GAT GCG CCT CAT GGT GAA             583
Ala Leu Glu Thr Gly Gly Asp Ile Leu Ile Asp Ala Pro His Gly Glu
     85                  90                  95

GCG TGG ATC CGT GAA GAC AGC GAT CGT TCA ATG TTA TTG ATT GCT GGC             631
Ala Trp Ile Arg Glu Asp Ser Asp Arg Ser Met Leu Leu Ile Ala Gly
```

5,484,723

|  |  |  |  |  |  |  |  |  |  |  |  |  |  |  |  |
|---|---|---|---|---|---|---|---|---|---|---|---|---|---|---|---|
| 100 |  |  |  |  | 105 |  |  |  |  | 110 |  |  |  |  | 115 |
| GGT | ACA | GGT | TTT | AGT | TAC | GTA | CTG | TCA | ATT | CTT | GAT | CAC | TGT | ATT | AGC | 679
| Gly | Thr | Gly | Phe | Ser | Tyr | Val | Leu | Ser | Ile | Leu | Asp | His | Cys | Ile | Ser |
|  |  |  |  | 120 |  |  |  |  | 125 |  |  |  |  | 130 |  |

```
CAA CAG ATT CAA AAA CCA ATT TAC CTA TAC TGG GGT GGT CGT GAT GAA     727
Gln Gln Ile Gln Lys Pro Ile Tyr Leu Tyr Trp Gly Gly Arg Asp Glu
            135             140             145

TGC CAA CTG TAT GCA AAA GCA GAA TTA GAG AGC ATT GCT CAA GCG CAT     775
Cys Gln Leu Tyr Ala Lys Ala Glu Leu Glu Ser Ile Ala Gln Ala His
            150             155             160

AGC CAT ATT ACG TTT GTG CCA GTG GTT GAG AAA AGT GAA GGC TGG ACA     823
Ser His Ile Thr Phe Val Pro Val Val Glu Lys Ser Glu Gly Trp Thr
    165             170             175

GGT AAA ACG GGT AAT GTG TTA GAA GCG GTA AAA GCC GAT TTT AAC TCA     871
Gly Lys Thr Gly Asn Val Leu Glu Ala Val Lys Ala Asp Phe Asn Ser
180             185             190             195

CTA GCA GAT ATG GAT ATT TAC ATC GCA GGT CGC TTT GAA ATG GCT GGT     919
Leu Ala Asp Met Asp Ile Tyr Ile Ala Gly Arg Phe Glu Met Ala Gly
            200             205             210

GCA GCA CGT GAG CAG TTC ACC ACT GAA AAA CAA GCG AAG AAA GAG CAG     967
Ala Ala Arg Glu Gln Phe Thr Thr Glu Lys Gln Ala Lys Lys Glu Gln
            215             220             225

CTG TTT GGT GAT GCA TTC GCA TTT ATC T  AATTTAGAGC ACTAAAAGA        1015
Leu Phe Gly Asp Ala Phe Ala Phe Ile
            230             235

CAAATAAAAA TGCCACTCAA TAATGAGTGG CATTTTTTA TGGATGTTAT AAAAAATGAA   1075

TTAGCCTTTA TCATCAACCA TAGTCAGTGC TTTACGAGAA AGATCT                 1121
```

( 2 ) INFORMATION FOR SEQ ID NO:6:

( i ) SEQUENCE CHARACTERISTICS:
( A ) LENGTH: 236 amino acids
( B ) TYPE: amino acid
( D ) TOPOLOGY: linear ( i i ) MOLECULE TYPE: protein ( x i ) SEQUENCE DESCRIPTION: SEQ ID NO:6:

```
Met Pro Ile Asn Cys Lys Val Lys Ser Ile Glu Pro Leu Ala Cys Asn
 1               5              10              15

Thr Phe Arg Ile Leu Leu His Pro Glu Pro Val Ala Phe Lys Ala
            20              25              30

Gly Gln Tyr Leu Thr Val Val Met Gly Glu Lys Asp Lys Arg Pro Phe
            35              40              45

Ser Ile Ala Ser Ser Pro Cys Arg His Glu Gly Glu Ile Glu Leu His
        50              55              60

Ile Gly Ala Ala Glu His Asn Ala Tyr Ala Gly Glu Val Val Glu Ser
65              70              75              80

Met Lys Ser Ala Leu Glu Thr Gly Gly Asp Ile Leu Ile Asp Ala Pro
            85              90              95

His Gly Glu Ala Trp Ile Arg Glu Asp Ser Asp Arg Ser Met Leu Leu
            100             105             110

Ile Ala Gly Gly Thr Gly Phe Ser Tyr Val Leu Ser Ile Leu Asp His
            115             120             125

Cys Ile Ser Gln Gln Ile Gln Lys Pro Ile Tyr Leu Tyr Trp Gly Gly
        130             135             140

Arg Asp Glu Cys Gln Leu Tyr Ala Lys Ala Glu Leu Glu Ser Ile Ala
145             150             155             160
```

```
Gln Ala His Ser His Ile Thr Phe Val Pro Val Val Glu Lys Ser Glu
            165             170             175

Gly Trp Thr Gly Lys Thr Gly Asn Val Leu Glu Ala Val Lys Ala Asp
            180             185             190

Phe Asn Ser Leu Ala Asp Met Asp Ile Tyr Ile Ala Gly Arg Phe Glu
        195             200             205

Met Ala Gly Ala Ala Arg Glu Gln Phe Thr Thr Glu Lys Gln Ala Lys
    210             215             220

Lys Glu Gln Leu Phe Gly Asp Ala Phe Ala Phe Ile
225             230             235
```

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..21

( x i ) SEQUENCE DESCRIPTION: SEQ ID NO:7:

```
CAR TAY YTN ATG GTN GTT ATG                                    21
Gln Tyr Leu Met Val Val Met
 1               5
```

( 2 ) INFORMATION FOR SEQ ID NO:8:

( i ) SEQUENCE CHARACTERISTICS:
        ( A ) LENGTH: 7 amino acids
        ( B ) TYPE: amino acids
        ( D ) TOPOLOGY: linear ( i i ) MOLECULE TYPE: protein ( x i ) SEQUENCE DESCRIPTION: SEQ ID NO:8:

```
Gln Tyr Leu Met Val Val Met
 1               5
```

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..20

( x i ) SEQUENCE DESCRIPTION: SEQ ID NO:9:

```
CGN CCN KCN AAR CTY TAC CG                                     20
Ala Gly Arg Phe Glu Met Ala
 1               5
```

( 2 ) INFORMATION FOR SEQ ID NO:10:

( i ) SEQUENCE CHARACTERISTICS:
        ( A ) LENGTH: 7 amino acids
        ( B ) TYPE: amino acids -continued (D) TOPOLOGY: linear (ii) MOLECULE TYPE: protein (xi) SEQUENCE DESCRIPTION: SEQ ID NO:10:

Ala Gly Arg Phe Glu Met Ala
 1               5